(12) United States Patent
Kim et al.

(10) Patent No.: US 7,777,894 B2
(45) Date of Patent: Aug. 17, 2010

(54) IMMERSION PHOTOLITHOGRAPHY MONITORING

(75) Inventors: Jae-Hyun Kim, Yongin-si (KR); Wang-Cheol Zin, Pohang-si (KR); Jung-Hoon Kim, Pohang-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 659 days.

(21) Appl. No.: 11/680,762

(22) Filed: Mar. 1, 2007

(65) Prior Publication Data

US 2008/0030693 A1 Feb. 7, 2008

(30) Foreign Application Priority Data

Aug. 3, 2006 (KR) .................. 10-2006-0073308

(51) Int. Cl.
*G01N 21/41* (2006.01)
*G01N 21/43* (2006.01)

(52) U.S. Cl. ...................................... 356/517
(58) Field of Classification Search ................. 356/128, 356/517
See application file for complete search history.

(56) References Cited

U.S. PATENT DOCUMENTS

| 6,844,206 | B1 | 1/2005 | Phan et al. |
| 6,999,254 | B1 | 2/2006 | Phan et al. |
| 7,006,209 | B2 | 2/2006 | Levinson |
| 7,215,431 | B2 * | 5/2007 | Opsal .......................... 356/630 |
| 7,483,117 | B2 * | 1/2009 | Hirukawa ..................... 355/30 |
| 2005/0237501 | A1 | 10/2005 | Furukawa et al. |
| 2005/0243292 | A1 | 11/2005 | Baselmans et al. |
| 2006/0139583 | A1 * | 6/2006 | Wegmann et al. ............. 355/30 |

FOREIGN PATENT DOCUMENTS

| JP | 2005-136404 | 5/2005 |
| JP | 2005-268412 | 9/2005 |
| JP | 2006-013130 | 1/2006 |
| KR | 10-2006-0058684 | 5/2006 |

* cited by examiner

*Primary Examiner*—Michael A Lyons
(74) *Attorney, Agent, or Firm*—F. Chau & Associates, LLC

(57) ABSTRACT

A method and apparatus are provided for monitoring an immersion photolithography process, the method including supplying an immersion fluid having an initial refractive index, performing photolithography using the supplied immersion fluid, recovering the used immersion fluid; and the apparatus including a light source, one or more fluid passageways disposed relative to the light source, and a light detector disposed on an opposite side of the fluid passageways relative to the light source for measuring a refractive index of a fluid in the fluid passageways.

16 Claims, 14 Drawing Sheets

IMMERSION PHOTOLITHOGRAPHY MONITORING

CROSS-REFERENCE TO RELATED APPLICATION

This application claims foreign priority under 35 U.S.C. §119 to Korean Patent Application No. 10-2006-0073308, filed on Aug. 3, 2006, in the Korean Intellectual Property Office, the disclosure of which is incorporated by reference herein in its entirety.

BACKGROUND OF THE INVENTION

As shown in FIGS. 1 and 2, an immersion photolithography apparatus is indicated generally by the reference numeral 100. The apparatus 100 may include a wafer stage 12, a wafer 14 disposed above the stage, a photo-resist ("PR") layer 16 disposed above the wafer, a fluid medium 18 disposed above the photo-resist, a lens 20 disposed above the medium, a lens module 22 disposed above the lens, and a light source 24 disposed above the lens module. The fluid medium 18 contacts both the lens 20 and the photo-resist 16. The apparatus 100 may further include a fluid supply tank 26 for supplying fluid to the fluid medium 18, and a fluid recovery tank 28 for recovering fluid from the fluid medium 18. The fluid supply tank contains and supplies a supply liquid 27, which is a substantially purified liquid having a refractive index n. The fluid recovery tank 28 recovers and contains a recovery liquid or suspension 29, which is the liquid plus additives or contaminants having a refractive index n'.

Here, the resolution R of the optical system is defined by:

$$R = \Lambda/NA \qquad \text{Eqn. 1}$$

$$NA = n \sin \Theta \qquad \text{Eqn. 2}$$

In Equations 1 and 2, $\Lambda$ is the wavelength of the main incident light, NA is the numerical aperture, n is the refractive index of the fluid medium between the lens module and the wafer, and $\Theta$ is the refracted angle between a central vertical axis of the lens module and the light going towards the focal point of the lens module from its edge region.

The NA is approximately in proportion to a diameter of the lens module and is approximately in inverse proportion to a focal distance d of the lens module. The resolution may be improved by increasing the refracted angle $\Theta$ or the refractive index n of the medium.

Conventional designs have required a design modification of the lens module to increase the refracted angle $\Theta$ for finer resolution. It has been proposed that the immersion photolithography apparatus may be supplied with an immersion liquid having a refractive index larger than that of air or vacuum between the lens module and the wafer. Unfortunately, because the immersion fluid directly contacts a photo-resist "photo-resist" layer of the wafer, an immersion liquid, particularly at the liquid to wafer boundary, may be contaminated by a photo acid generator ("PAG") of the photo-resist. Thus, if some PAG contaminates the immersion liquid, the refractive index may be undesirably varied by the PAG, and the lens and/or lens module may be undesirably corroded by the PAG.

In addition, the refractive index of the immersion liquid varies according to the temperature of the liquid. For example, as the temperature of the immersion liquid rises, the density of the immersion liquid decreases, and, in turn, the refractive index of the immersion liquid also decreases. In cases where the refractive index of the immersion liquid varies for any reason, it may prevent the formation of a uniform and refined photo-resist pattern on the wafer. A detection system has been proposed in which contaminants of the fluid medium between the lens and the wafer would be measured directly. See, e.g., U.S. Pat. No. 7,006,209. Unfortunately, such systems may not be usable with some simultaneous real-time photolithography processes because of interference between the detectors light output, the main light source, and local reflections. In addition, the single pass refraction of the detecting light through the liquid may result in a coarse measurement. Further, the system fails to account for the non-uniform distribution of the contaminants, at least the heavier of which may be more concentrated near their source at the boundary between the wafer and the liquid medium.

SUMMARY OF THE INVENTION

These and other issues are addressed by a method, apparatus and system for immersion photolithography. Exemplary embodiment methods, apparatus and systems are provided.

An exemplary method for monitoring an immersion photolithography process includes supplying an immersion fluid having an initial refractive index, performing photolithography using the supplied immersion fluid, recovering the used immersion fluid, and monitoring the refractive index of the recovered immersion fluid.

An exemplary apparatus for monitoring an immersion photolithography process includes a light source, one or more fluid passageways disposed relative to the light source, and a light detector disposed on an opposite side of the fluid passageways relative to the light source for measuring a refractive index of a fluid in the fluid passageways.

An exemplary system for monitoring an immersion photolithography process includes an immersion fluid monitoring apparatus, a controller coupled in signal communication with the immersion fluid monitoring apparatus for controlling the photolithography system in response to a refractive index of an immersion fluid as measured by the immersion fluid monitoring apparatus, an immersion hood coupled in fluid communication with the immersion fluid monitoring apparatus, a wafer stage disposed below the immersion hood for supporting a semiconductor wafer, a photolithography light source coupled in signal communication with the controller, a projection lens optically aligned between the photolithography light source and the wafer stage, an immersion fluid supply nozzle disposed on the immersion hood for supplying an immersion fluid between the projection lens and a layer on the semiconductor wafer, and an immersion fluid recovery conduit disposed on the immersion hood for recovering the immersion fluid, wherein the immersion fluid monitoring apparatus is coupled in fluid communication with the recovery conduit.

The present disclosure will be further understood from the following description of exemplary embodiments, which is to be read in connection with the accompanying drawings.

BRIEF DESCRIPTION OF THE DRAWINGS

The present disclosure presents an apparatus and method for immersion photolithography in accordance with the following exemplary figures in which.

DETAILED DESCRIPTION OF PREFERRED EMBODIMENTS

An immersion photolithography apparatus, refractive index monitoring unit for monitoring an immersion fluid, and a method of monitoring an immersion photolithography process are provided. An immersion photolithography apparatus has a monitoring unit for monitoring the refractive index of an immersion fluid.

An apparatus includes a supply nozzle for supplying the immersion fluid onto a wafers a recovery nozzle for recovering immersion fluid from the wafer, and a refractive index monitoring unit connected to the recovery nozzle. The refractive index monitoring unit includes an auxiliary light source and a light detector located on opposite sides of a recovery fluid tank or passageway. The auxiliary light source generates auxiliary light passing through the recovery fluid. The auxiliary light includes an incident light component entering the recovery fluid and a refracted light component exiting the recovery fluid. The light detector measures an intensity gradient or displacement of the refracted light when the incident light is applied.

Figure 1:
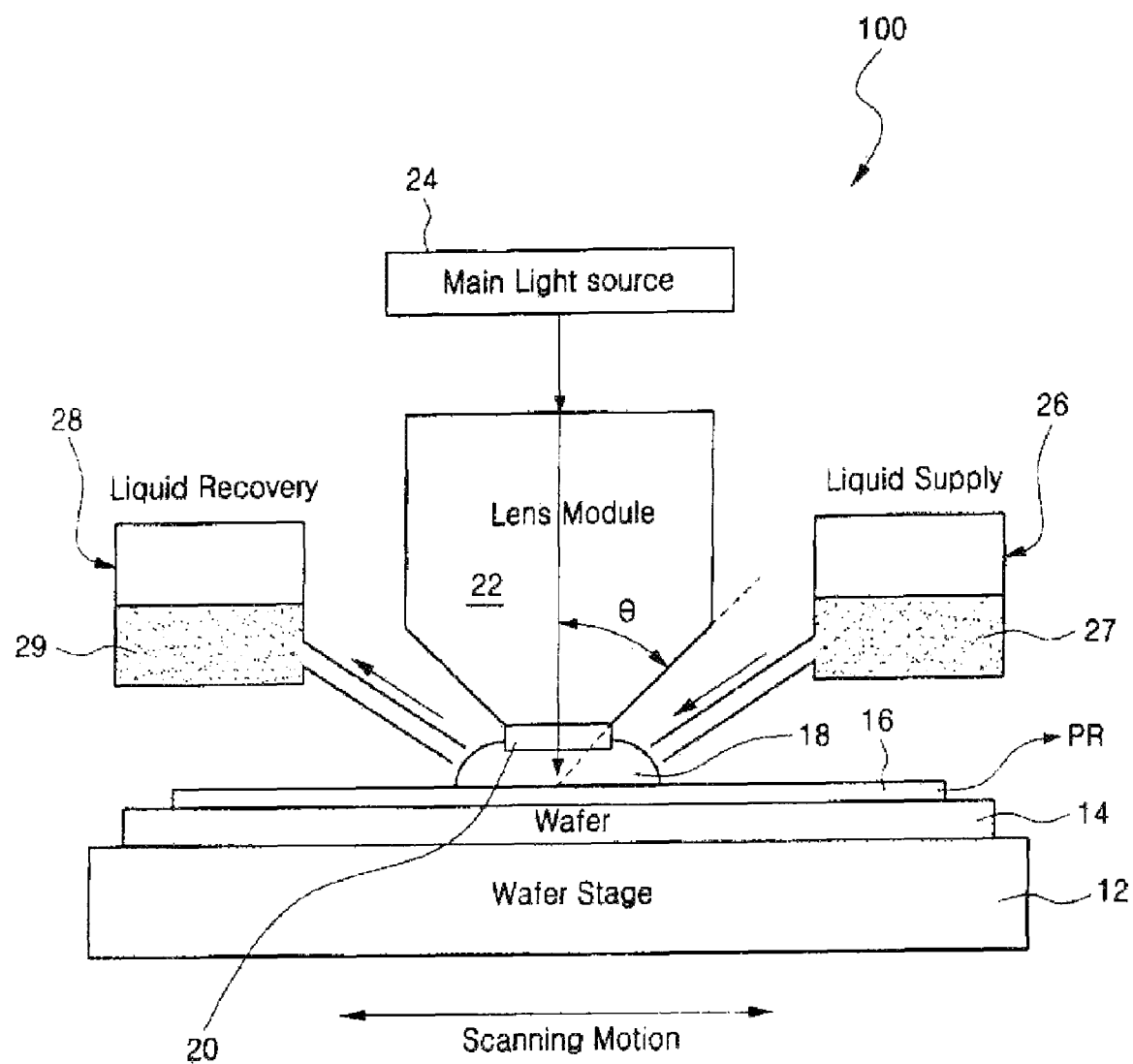
FIG. 1 shows a schematic diagram for an immersion photolithography apparatus.
Figure 2:
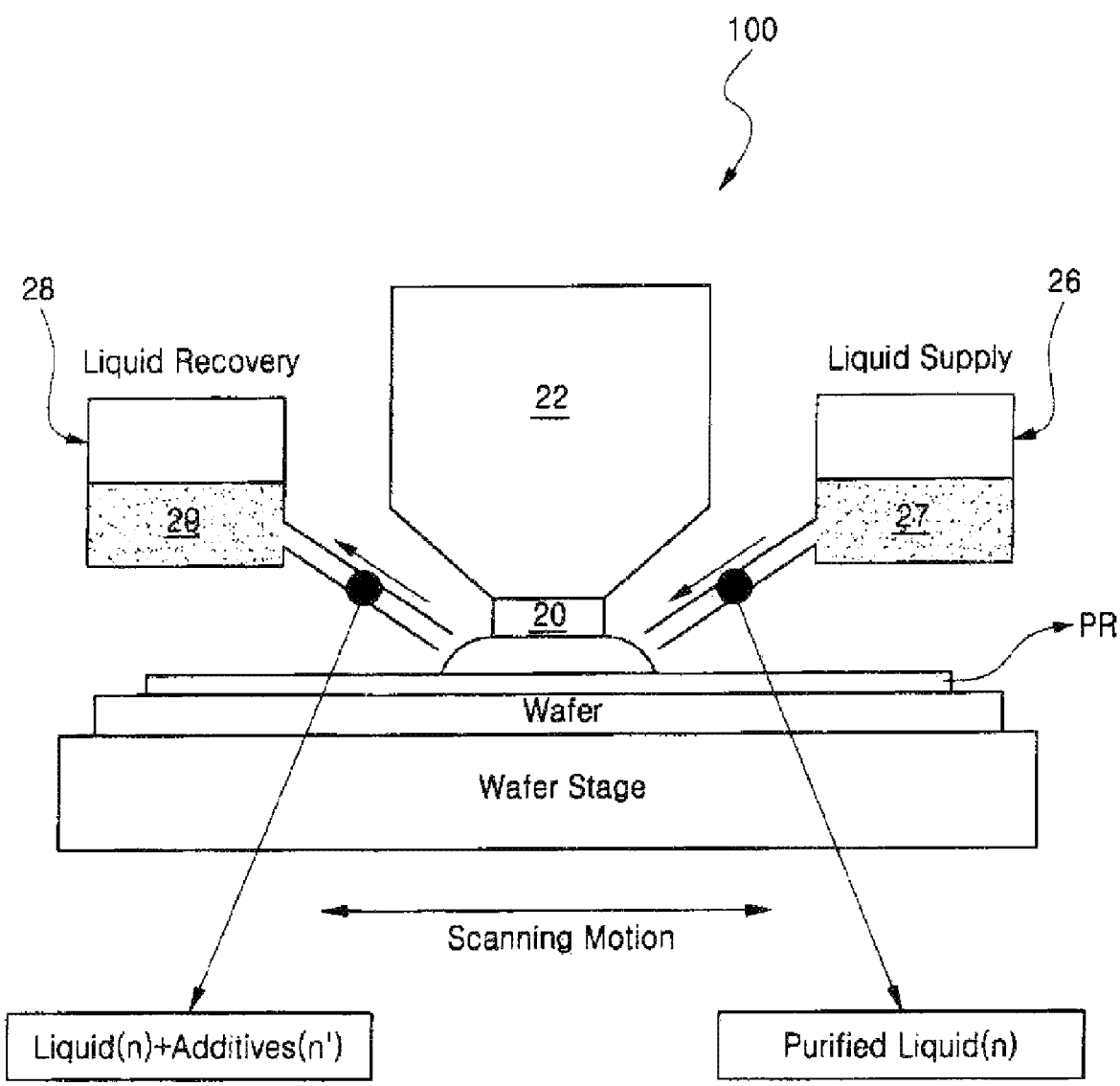
FIG. 2 shows a schematic diagram for the immersion photolithography apparatus of FIG. 1.
Figure 3:
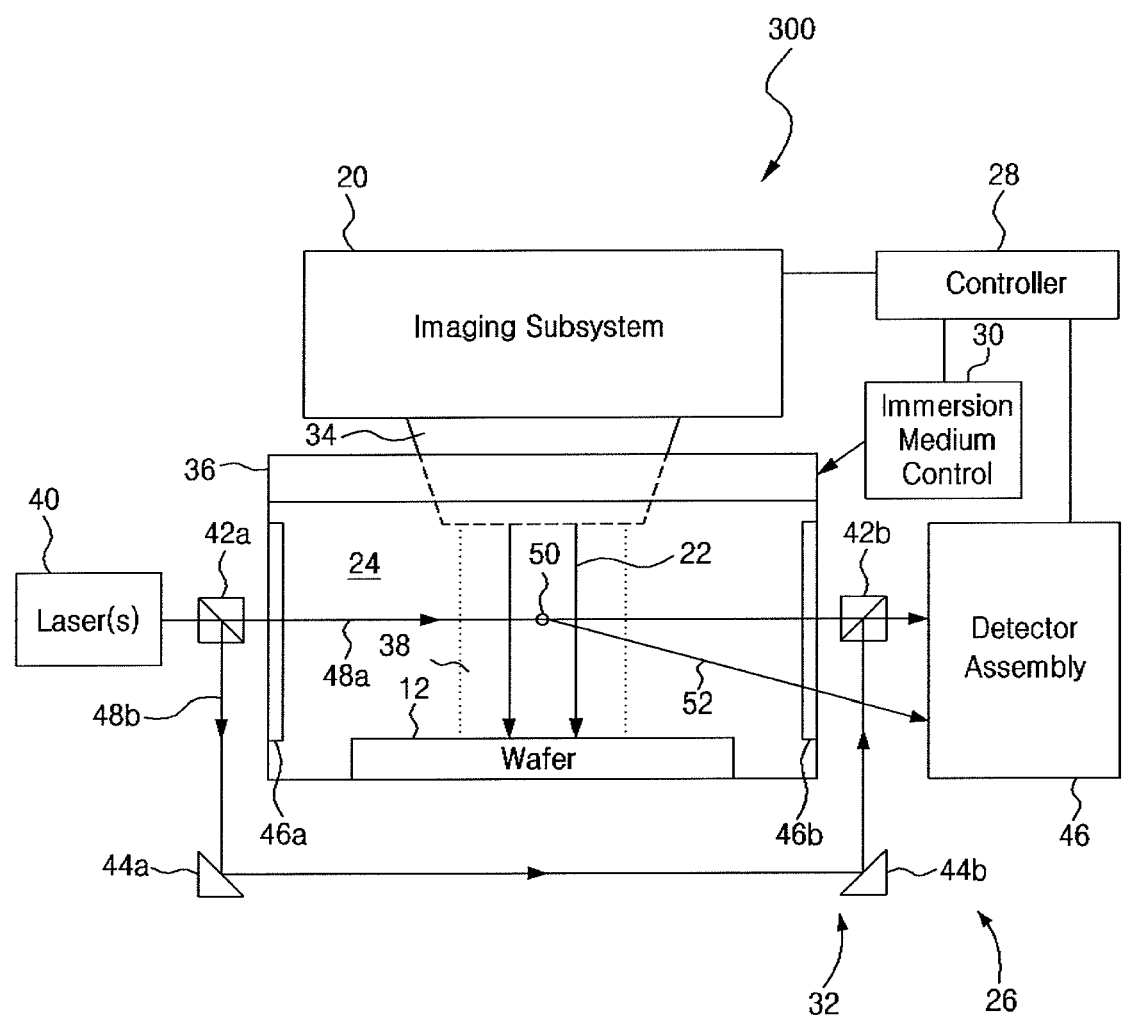
FIG. 3 shows a schematic diagram for an immersion photolithography system.

As shown in FIG. 3, an immersion photolithography system is indicated generally by the reference numeral 300. The system 300 includes an immersion liquid 24, such as de-ionized water, a medium chamber 36 filled with the immersion liquid that contacts a wafer, beam splitters 42a and 42b, a first light component 48a passing through the immersion liquid, a second light component 48b bypassing the liquid, a foreign body 50, and scattered light 52.

The system 300 monitors a refractive index of the immersion liquid by comparing the first light component 48a with the second light component 48b. It does so by measuring a phase difference or a frequency difference between the first and second light components.

Figure 4:
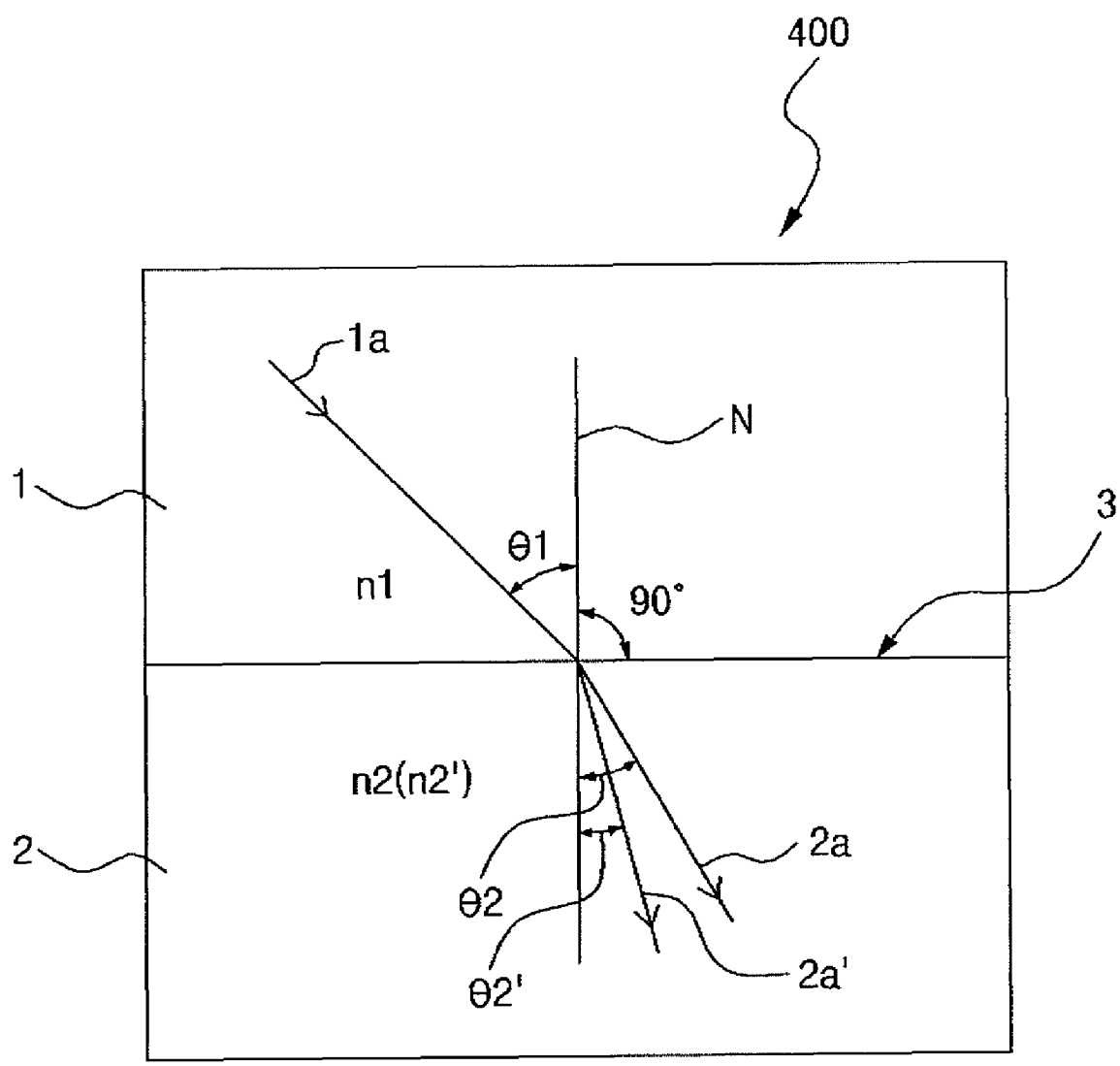
FIG. 4 shows a graphical diagram for a refraction angle of an immersion photolithography apparatus.

Turning to FIG. 4, a plot of refraction angle is indicated generally by the reference numeral 400. A first medium 1 meets a second medium 2 at an interface 3. Here, n1 is a first refractive index of the first medium 1, n2 is a second refractive index of the second medium 2, 1a is the incident light, N is a Normal line, $\Theta 1$ is an incident angle between N and 1a, 2a is the refracted light, and $\Theta 2$ is the refracted angle between N and 2a.

According to Snell's law:

$$n1 < n2 \rightarrow \Theta 1 > \Theta 2 \qquad \text{Eqn. 3}$$

$$n2 < n2' \rightarrow 2 > \Theta 2' \qquad \text{Eqn. 4}$$

Thus, as the refractive index n2' of the medium increases, the refraction angle $\Theta 2'$ decreases for refracted light 2a' passing through the medium.

Figure 5:
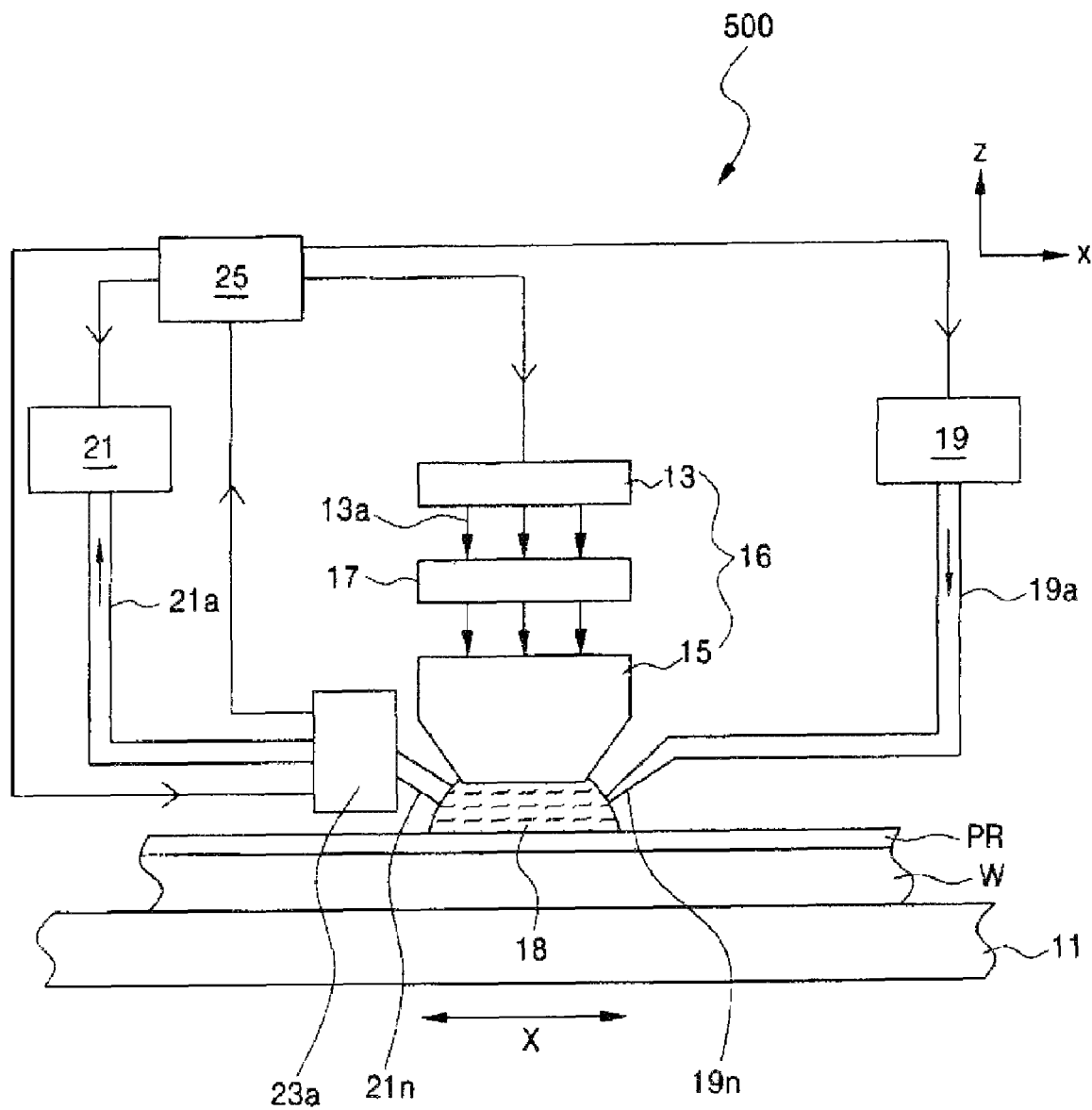
FIG. 5 shows a schematic diagram for an immersion photolithography apparatus in accordance with an exemplary embodiment of the present disclosure.

Turning now to FIG. 5, an immersion photolithography apparatus in accordance with an exemplary embodiment of the present disclosure is indicated generally by the reference numeral 500. The apparatus 500 includes a wafer stage 11, a wafer ("W") on the wafer stage, a photo-resist ("PR") layer on the wafer, an immersion liquid ("IL") medium 18 on the photo-resist layer, an optical system 16 disposed above the IL medium 18, a main light source 13 disposed near the top of the optical system, a lens module 15 disposed near the bottom of the optical system, main light 13a emitted by the light source 13, a photo mask 17 below the main tight source for receiving the main light, an immersion liquid supply part 19, an immersion liquid supply pipe 19a connected to the supply part 19, an immersion liquid supply nozzle 19n for supplying immersion liquid to the medium 18, a recovery nozzle 21n for recovering used immersion liquid from the medium 18, an immersion liquid recovery pipe 21a connected to the recovery nozzle, an immersion liquid recovery part 21 connected to the recovery pipe, a temperature-controlled immersion liquid refractive index monitoring unit 23a connected to the recovery pipe 21a, and a controller 25 in signal communication with the monitoring unit 23a. The controller 25 is further in signal communication with each of the supply part 19, the recovery part 21, and the light source 13.

In this embodiment, the wafer stage 11 is located under the optical system 16, and is movable in x, y, and z directions, allowing the wafer W, coated with photo-resist layer, to be loaded. The optical system 16 comprises the main light source 13 and the lens module 15. The main light source 13 generates the main light 13a, which is projected towards the photo-resist layer on the wafer W through the photo-mask 17, the lens module 15, and the IL medium 18. The supply part 19 supplies the IL medium on the photo-resist with immersion liquid through the supply pipe 19a and the supply nozzle 19n. The immersion liquid comprises a liquid having a refraction index above about 1, such as de-ionized water, for example. The immersion liquid fills the space between the lens module 15 and the photo-resist, thereby forming an IL medium 18 to increase the resolution of the optical system.

The monitoring unit 23a is connected to the recovery part 21 through the recovery pipe 21a, which is located after the recovery nozzle 21n and the lens module 15. The recovery part 21 recovers the used immersion liquid from the immersion liquid on the wafer through the recovery nozzle 21n, the monitoring unit 23a, and the recovery pipe 21a as the IL medium 18 on the photo-resist is supplied through the supply nozzle 19n. If the immersion liquid is contaminated by a chemical contained in the photo-resist, the immersion liquid on the recovery side of the medium 18 may have a different refractive index as compared to the immersion liquid on the supply side of the medium in the supply pipe 19a, for example. In cases where the refractive index is changed, a most suitable condition for exposing the photo-resist may be affected because a focal distance of the lens module 15 is changed.

The exemplary monitoring unit 23a measures an intensity of the refracted light passing through the immersion liquid recovered through the recovery nozzle 21n, and generates an electric output signal corresponding to the refracted light intensity. The monitoring unit 23a is designed to make the output signal change as the refractive index of the recovered immersion liquid changes. The output signal is sent to the controller 25, which calculates the refractive index of the recovered immersion liquid using the output signal of the monitoring unit 23a. In case a permitted limit of the refractive index of the recovered immersion liquid is reached, the controller 25 may stop at least one of the operations of the supply part 19, the recovery part 21, the main tight source 13, or the wafer stage 11.

Figure 6:
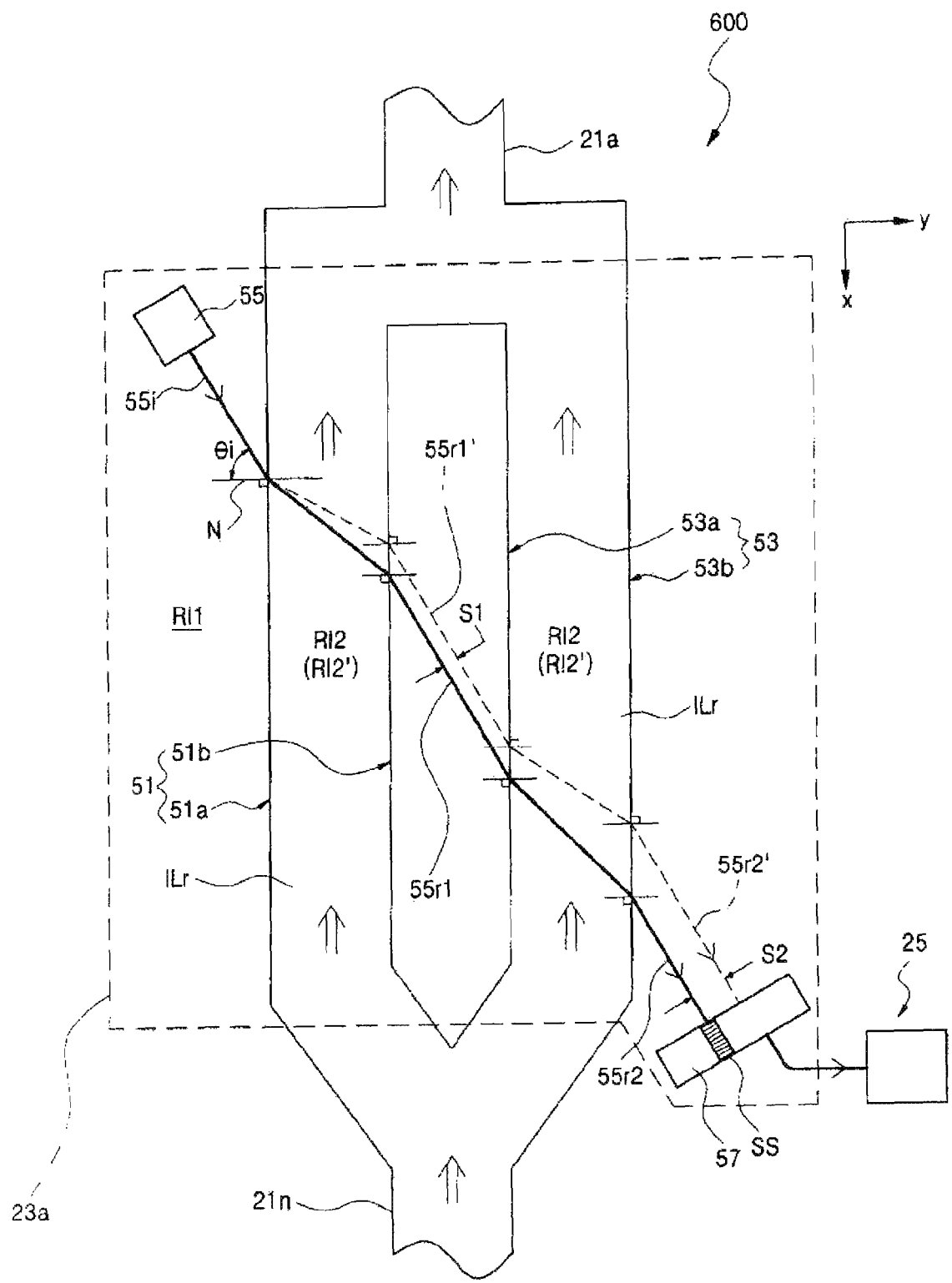
FIG. 6 shows a schematic diagram for a refractive index monitoring unit in accordance with the immersion photolithography apparatus of FIG. 5.

As shown in FIG. 6, an exemplary refractive index monitoring unit, usable in accordance with the immersion photolithography apparatus of FIG. 5, is indicated generally by the reference numeral 600. Here, a portion 23a of the unit 600 may be used in the apparatus 500 of FIG. 5. The monitoring unit 600 includes a first recovery conduit 51, which may be disposed between the recovery nozzle 21n and the recovery pipe 21a of the apparatus 500 of FIG. 5, and a second recovery conduit 53 disposed in parallel with the first conduit 51.

The monitoring unit 600 further includes an auxiliary tight source 55 disposed on one side of the parallel conduits 51 and 53, and a light detector 57 disposed on an opposite side of the parallel conduits 51 and 53. The conduit 51 includes its own first and second recovery sidewalls 51a and 51b, respectively. The conduit 53 also includes its own first and second recovery sidewalls 53a and 53b, respectively. The conduits each contain a flow of recovered immersion liquid ("ILr").

The auxiliary light source 55 provides an auxiliary incident beam of light 55i through a first material, such as air, having a first refractive index of RI1, to the sidewall 51a. The light transmitted at the sidewall 51a passes through the recovered immersion liquid having a second refractive index, initially or normally of RI2, to the sidewall 51b. A first reference refracted beam of light 55r1 transmitted at the sidewall 51b passes through more of the first material to the sidewall 53a. The light transmitted at the sidewall 53a passes through more of the recovered immersion liquid to the sidewall 53b. A second reference refracted beam of light 55r2 transmitted at the sidewall 53b passes through more of the first material to the light detector 57.

As the composition of the recovered immersion liquid changes due to contamination, its refractive index changes from RI2 to RI2'. The light transmitted at the sidewall 51a passes through the recovered immersion liquid having a second refractive index, abnormally of RI2', to the sidewall 51b. A first abnormal refracted beam of light 55r1' transmitted at the sidewall 51b passes through more of the first material to the sidewall 53a. The tight transmitted at the sidewall 53a passes through more of the recovered immersion liquid to the sidewall 53b. A second abnormal refracted beam of light 55r2' transmitted at the sidewall 53b passes through more of the first material to the light detector 57.

Thus, the exemplary monitoring unit 600 comprises the auxiliary light source 55, the light detector 57, and at least two recovery conduits 51 and 53. The first and second recovery conduits 51 and 53 are arranged between the auxiliary light source 55 and the light detector 57. A first common end of the first and second recovery conduits 51 and 53 is connected to the recovery nozzle 21n, and a second common end of the first and second recovery conduits 51 and 53 is connected to the recovery pipe 21a. The first recovery conduit 51 has first and second recovery sidewalls 51a and 51b, and the second recovery conduit 53 has first and second recovery sidewalls 53a and 53b.

Here, the recovery sidewalls are arranged in parallel with each other, and may be horizontally or vertically oriented. When the immersion liquid from the medium on the wafer is recovered into the first and second recovery conduits 51 and 53 through the recovery nozzle 21n, an auxiliary light irradiated from the auxiliary light source 55 is refracted towards the light detector 57 through the two pairs of first and second recovery sidewalls 51a, 51b, 53a, and 53b, and through the recovered immersion liquid within the conduits 51 and 53.

If the adjacent fluid medium outside of the first and second recovery conduits 51 and 53 has a first refractive index RI1, and the recovered immersion liquid that is recovered into the first and second recovery conduits 51 and 53 has a second refractive index RI2 or RI2' that is larger than the first refractive index RI1, the auxiliary tight is refracted whenever the auxiliary light passes through the first and second recovery sidewalls in accordance with Snell's law. The incident angle $\Theta i$ corresponds to the angle between the normal line being vertical to the first recovery conduit sidewall 51a of the first recovery conduit 51, and the auxiliary incident light 55i. The adjacent medium may be a vacuum or air, for example, having a refractive index of about 1, and the immersion fluid is a liquid having a refractive index above 1, such as de-ionized water.

If the immersion liquid ("IL") contacting the wafer is not contaminated, the recovered immersion liquid ("ILr") recovered into the first and second recovery conduits 51 and 53 has the same refractive index as the second refractive index RI2 of the immersion liquid in the supply pipe 19a. In this case, the auxiliary light comprises the auxiliary incident light 55i, the first reference refracted light 55r1 projected towards the first recovery sidewall 53a of the second recovery conduit 53 through the first recovery conduit 51, and the second reference refracted light 55r2 projected towards the light detector 57 through the second recovery conduit 53.

If, on the other hand, the immersion liquid contacting the wafer is contaminated, such as by a photo acid generator ("PAG") of the photo-resist, the immersion liquid ILr recovered into the first and second recovery conduits 51 and 53 has a second abnormal refractive index RI2' larger than the second refractive index RI2 of the immersion liquid into the supply pipe 19a.

In this case, the auxiliary light comprises the auxiliary incident light 55i, the first abnormal refracted light 55r1' projected towards the first recovery sidewall 53a of the second recovery conduit 53 through the first recovery conduit 51 and the second abnormal refracted light 55r2' projected towards the light detector 57 through the second recovery conduit 53.

The light detector 57 may comprise a light sensor ("SS") detecting an intensity of the second reference refracted light 55r2 or the second abnormal refracted light 55r2'. The paths of the first and second abnormal refracted lights 55r1', 55r2' may differ from those of the first and second reference refracted lights 55r1, 55r2, respectively, because the second abnormal refracted index RI2' of the contaminated liquid differs from the refractive index RI2 of the non-contaminated immersion liquid.

An exemplary light sensor SS of the light detector 57 is located in a position that shows the highest intensity of the second reference refracted light 55r2, and therefore the light intensity detected by the light detector varies according to the refracted light of the immersion liquid ILr recovered into the recovery conduits 51 and 53. That is, as the contaminant level in the recovered immersion liquid ILr increases, the light intensity detected by the light detector 57 decreases.

The intensity of the second refracted light 55r2 or 55r2' detected by the light detector 57 is transferred to the controller 25 in from of an electric signal. The controller 25, in turn, calculates a refractive index of the immersion liquid ILr recovered into the recovery conduits 51 and 53 using the output signal of the light detector 57. When a refractive index of the recovered immersion liquid ILr deviates from a permitted limit, the controller 25 controls at least one operation of the supply part 19, the recovery part 21, the main light source 13 and the wafer stage 11.

According to Snell's law, a gap S2 between the second reference refracted light 55r2 and the second abnormal refracted light 55r2' may be larger than a gap S1 between the first reference refracted light 55r1 and the first abnormal refracted light 55r1'. Therefore, as the number of recovery conduits increases, even though the refractive index of the recovered immersion liquid ILr may vary only slightly, it is possible to accurately measure and calculate the variation of the refractive index of the recovered immersion liquid ILr to a very fine degree.

Figure 7:
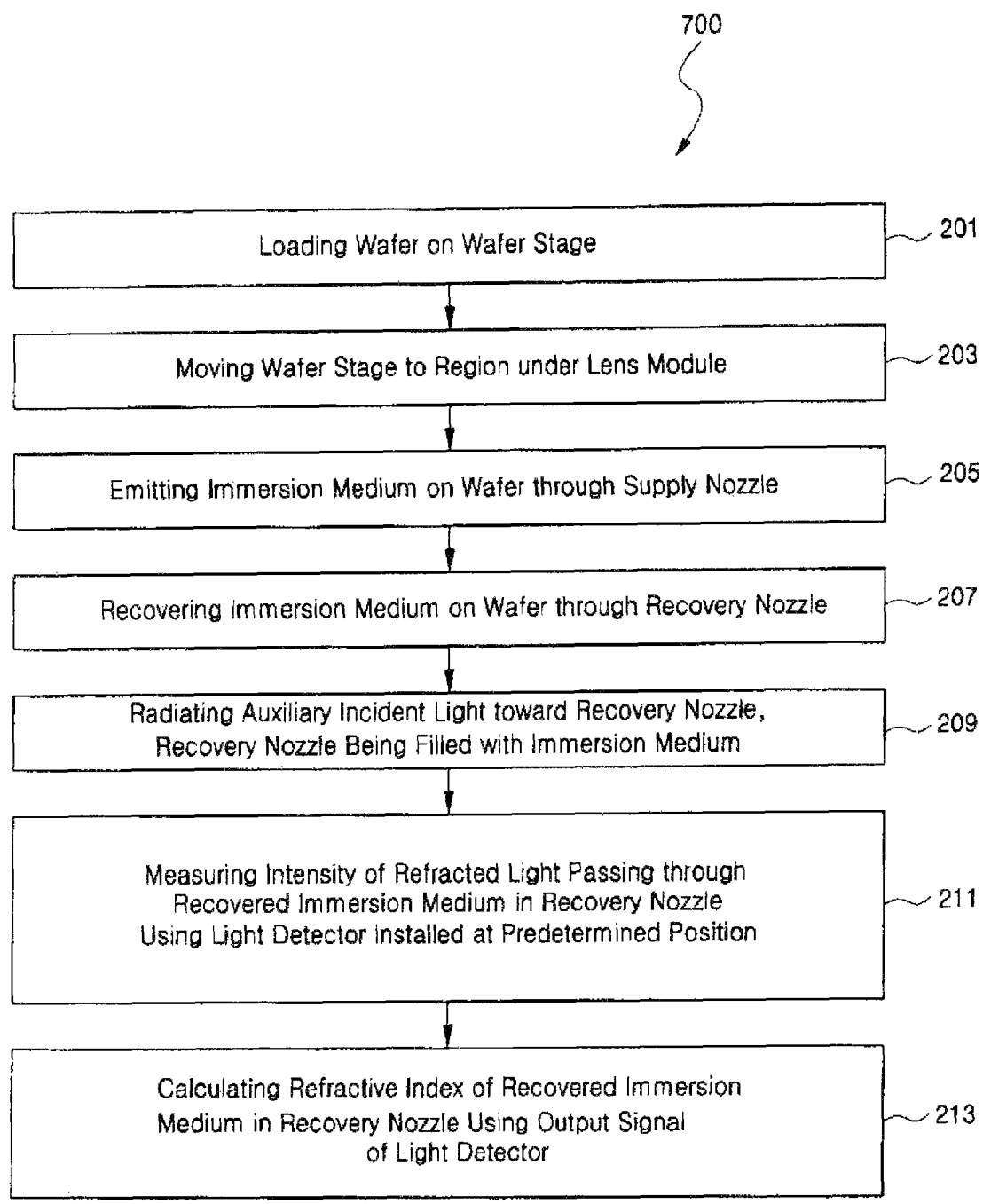
FIG. 7 shows a flowchart for an immersion photolithography method in accordance with an exemplary embodiment of the present disclosure.

Turning to FIG. 7, a flowchart for a method of monitoring the immersion photolithography apparatus 500 of FIG. 5 is indicated generally by the reference numeral 700. The method 700 measures in real-time the refractive index of the immersion liquid using the immersion photolithography monitoring unit 23a of FIG. 5.

The method 700 includes a function block 201 in which a wafer W coated by photo-resist is loaded onto the wafer stage 11. The function block 201 passes control to a function block 203, in which the wafer stage 11 loading the wafer W is moved under the lens module 15 of the optical system 16. Next, control is passed to a function block 205, in which the immersion liquid is injected towards a space between the lens module 15 and the wafer W through the supply nozzle 19n. The function block 205, in turn, passes control to a function block 207. During the injection of the immersion liquid, the function block 207 recovers the immersion liquid supplied on the wafer W through the recovery nozzle 21n, and thence through the recovery conduits such as 51 and 53 of FIG. 6.

The block 207 passes control to a function block 209. During the recovery of the immersion from the wafer W into the recovery conduits 51 and 53, the function block 209 projects an auxiliary incident light 55i towards the first recovery conduit sidewall 51a of the first recovery conduit 51, for example. Next, when the auxiliary incident light 55i is irradiated on the first recovery sidewall 51a, the refracted light 55r2 or 55r2' is generated passing through the immersion liquid ILr recovered into the first and second recovery conduits 51 and 53. A function block 211 measures the intensity of the refracted light 55r2 or 55r2' using the light detector 57.

The function block 211 passes control to a function block 213. The path of the refracted light 55r2 or 55r2' varies according to the size of the refractive index of the immersion liquid recovered into the recovery conduits 51 and 53. The light detector 57 can generate the electrical output signal corresponding to the refracted light intensity. The function block 213 transmits the output signal to an input terminal and the controller 25 calculates a refractive index of the recovered immersion liquid using the output signal. When the refractive index of the recovered immersion liquid deviates from the permitted limit, the controller 25 can control the operation of the immersion photolithography apparatus.

Figure 8:
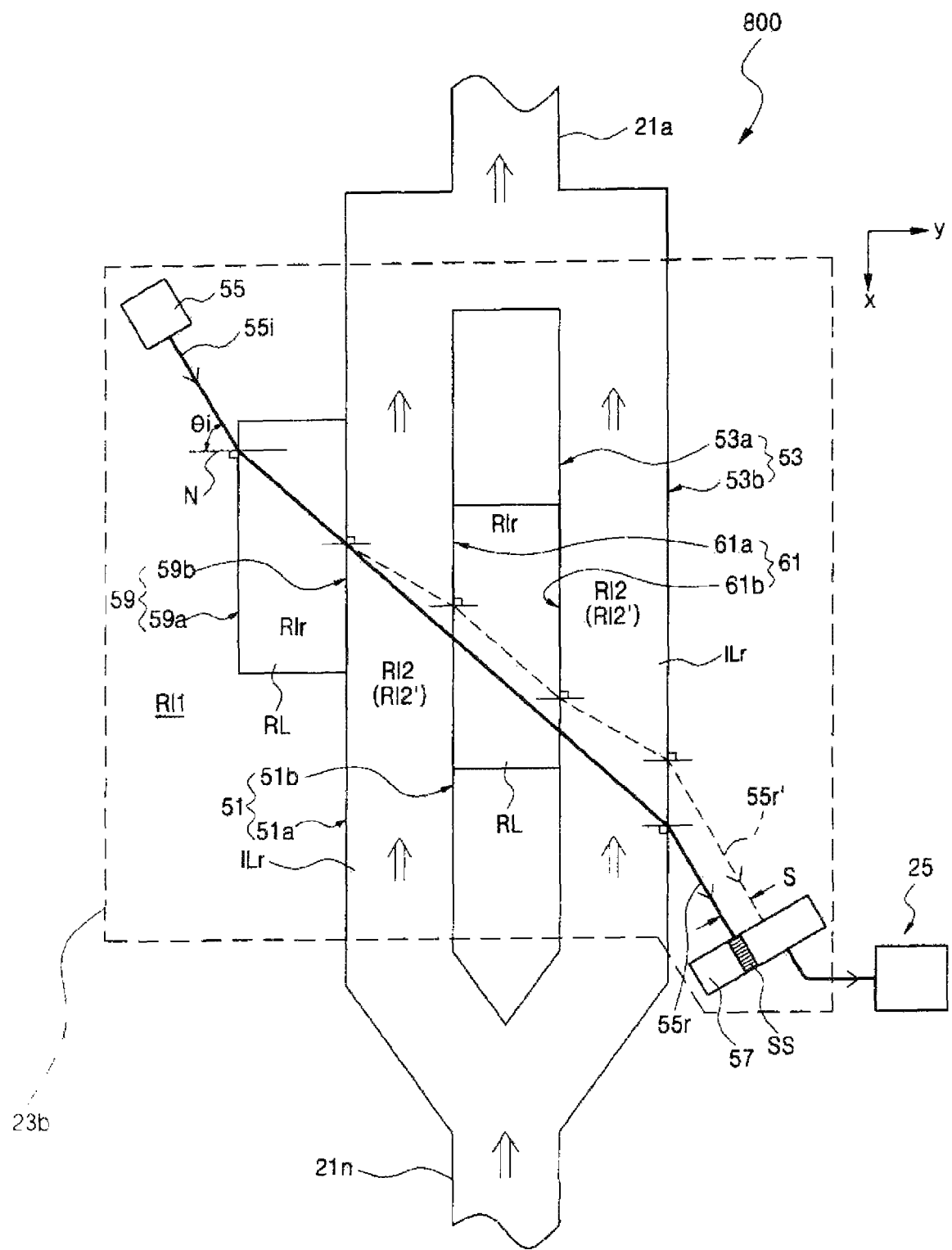
FIG. 8 shows a schematic diagram for another refractive index monitoring unit in accordance with the immersion photolithography apparatus of FIG. 5.

Turning now to FIG. 8, another exemplary refractive index monitoring unit embodiment is indicated generally by the reference numeral 800. The monitoring unit 800 is similar to the monitoring unit 600 of FIG. 6, but includes a first reference liquid conduit disposed between the light source and the first recovery liquid conduit, and a second reference liquid conduit disposed between the first recovery liquid conduit and the second recovery liquid conduit. Thus, the unit 800 includes a portion 23b, which may be used as the unit 23a of the apparatus 500 of FIG. 5. The refractive index monitoring unit 800 includes a first reference vessel or conduit 59 having a first reference sidewall 59a and a second reference sidewall 59b, a second reference vessel or conduit 61 having a first reference sidewall 61a and a second reference sidewall 61b, a reference liquid RL having a reference refractive index RIr, a referenced refracted light beam 55r and an abnormal referenced refracted light beam 55r'.

Here, the monitoring unit 23b includes the first reference vessel 59 and the second reference vessel 61. The first reference vessel 59 comprises a first reference sidewall 59a and a second reference sidewall 59b, which are located in parallel with each other. The second reference vessel 61 comprises a first reference sidewall 61a and a second reference sidewall 61b, which are also located in parallel with each other. The first and second pairs of reference sidewalls 59a and 59b, and 61a and 61b, which may be perpendicular to the x-y plane, are parallel to the first and second pairs of recovery sidewalls 51a and 51b, which may be parallel to the x-y plane.

The reference vessels 59 and 61 are filled with a reference medium RL having a reference refractive index RIr. The refractive index RIr of the reference medium RL may be same to the second refractive index RI2 of the immersion liquid in the supply pipe 19a, for example.

The auxiliary light reaches the light detector 57 through the pairs of first and second sidewalls 59a and 59b, 51a and 51b, 61a and 61b, and 53a and 53b, where there is reference liquid RI in the first and second reference vessels 59 and 61, and the recovered immersion liquid ILr in the first and second recovery conduits 51 and 53.

If the immersion liquid supplied on the wafer is not contaminated, the immersion liquid ILr recovered into the first and second recovery conduits 51 and 53 has the same refractive index with the second refractive index RI2 of the immersion liquid in the supply pipe 19a. In this case, the auxiliary light comprises the auxiliary incident light 55i, the reference refracted light 55r irradiated toward the light detector 57 through the reference vessels 59 and 61 and the recovery conduits 51 and 53.

If the immersion liquid supplied on the wafer is contaminated by a photo acid generator ("PAG") of the photo-resist, the immersion liquid ILr recovered into the first and second recovery conduits 51 and 53 has a second abnormal refractive index RI2' larger than the second normal refractive index RI2 of the immersion liquid in the supply pipe 19a. In this case, the auxiliary light comprises the auxiliary incident light 55i, and the abnormal refracted light 55r' irradiated toward the light detector 57 through the reference vessels 59 and 61 and the recovery conduits 51 and 53.

Figure 9:
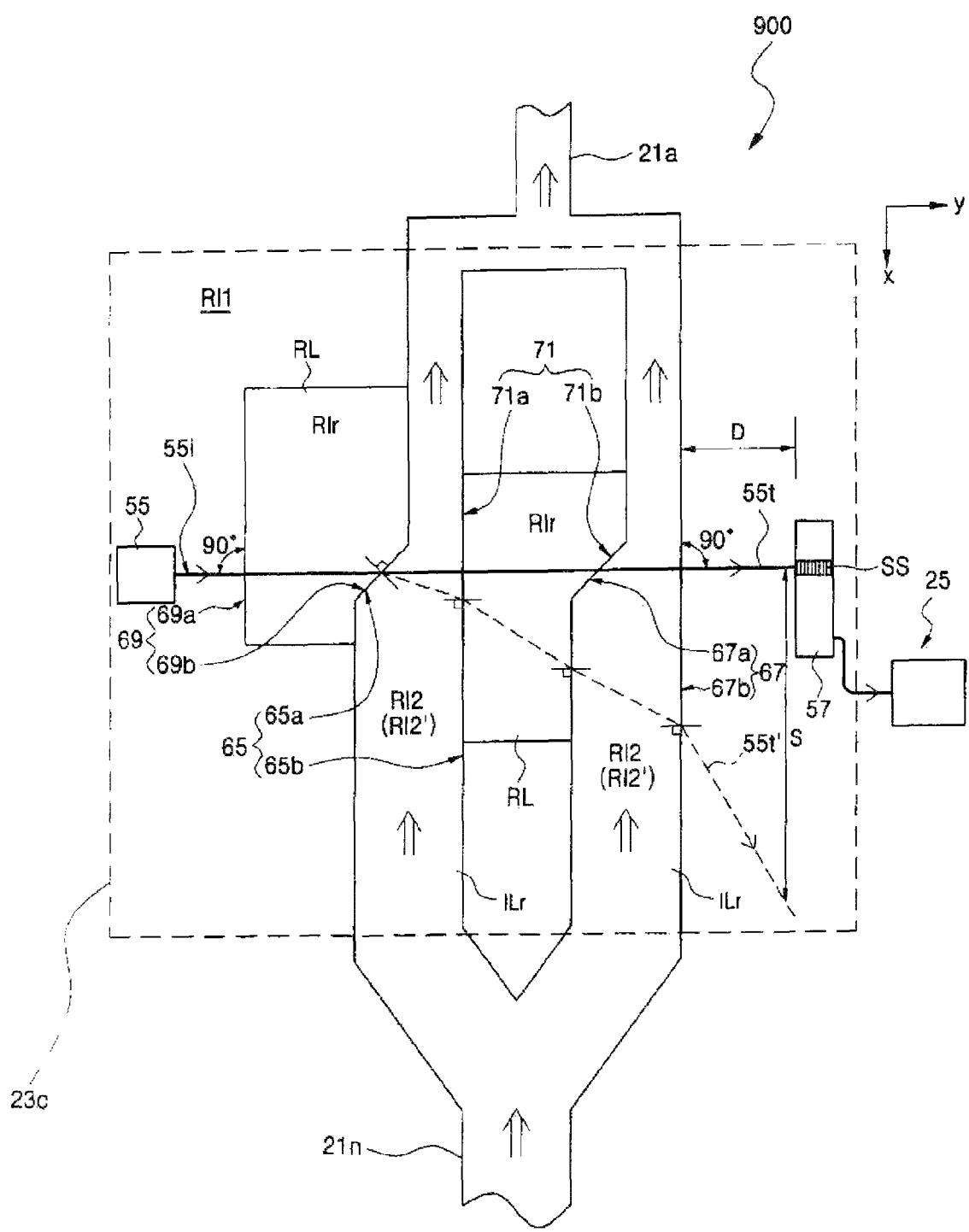
FIG. 9 shows a schematic diagram for another refractive index monitoring unit in accordance with the immersion photolithography apparatus of FIG. 5.

As shown in FIG. 9, another exemplary refractive index monitoring unit embodiment is indicated generally by the reference numeral 900. The monitoring unit 900 is similar to the monitoring unit 800 of FIG. 8, but the first sidewall of the first recovery conduit and the first sidewall of the second recovery conduit are disposed at an acute angle relative to their second sidewalls, respectively.

The monitoring unit 900 includes a monitoring portion 23c, first and second recovery conduits 65 and 67, first and second reference vessels 69 and 71, first recovery sidewalls 65a and 67a, second recovery sidewalls 65b and 67b, first reference sidewalls 69a and 71a, and second reference sidewalls 69b and 71b.

The monitoring unit 900 differs from the monitoring unit 800 in the shapes of the recovery conduits and the reference vessels. The first recovery conduit 65 comprises first and second recovery sidewalls 65a and 65b, which are non-parallel to each other. The second recovery conduit 67 also comprises first and second recovery sidewalls 67a and 67b, which are non-parallel to each other.

The first reference vessel 69 comprises a first reference sidewall 69a and a second reference sidewall 69b, which are non-parallel to each other. The second reference vessel 71 comprises a first reference sidewall 71a and a second reference sidewall 71b, which are non-parallel to each other. The first reference sidewalls 69a and 71a, and the second recovery sidewalls 65b and 67b are all substantially parallel to each other. The second reference sidewalls 69b and 71b and the first recovery sidewalls 65a and 67a also are substantially parallel to each other.

The reference vessels 69 and 71 are filled with a reference liquid or medium RL having a reference refractive index RIr. The refractive index RIr of the reference medium RL may be same as the second refractive index RI2 of the immersion liquid in the supply pipe 19a. The auxiliary light reaches the light detector 57 through the reference medium RL in the reference vessels 69 and 71, and through the immersion liquid ILr recovered in the recovery conduits 65 and 67.

If the immersion liquid supplied on the wafer is not contaminated, the immersion liquid ILr recovered into the first and second recovery conduits 65 and 67 has the same refractive index as the second refractive index RI2 of the immersion liquid in the supply pipe 19a. In this case, the auxiliary light comprises the auxiliary incident light 55i, the reference output light 55t irradiated toward the light detector 57 through the reference vessels 69 and 71 and the recovery conduits 65 and 67.

The incident angle of the auxiliary incident tight 55i is 0° and even though the auxiliary light is irradiated obliquely toward the second reference sidewall 69b, the auxiliary light goes straight ahead to the light detector 57 without deviation due to refraction.

If the immersion liquid supplied on the wafer is contaminated to cause a larger refractive index than that of the reference medium RL, the auxiliary light is refracted adjacent to the interface between the reference medium RL and the recovered immersion liquid ILr along the path as indicated by a dotted line for 55t'. In this case, the auxiliary light comprises the auxiliary incident light 55i and the refracted light 55t' irradiated toward the light detector 57.

If a distance D between the light detector 57 and the second recovery conduit 67 increases, a gap S between the reference output light 55t and the refracted light 55t' increases. So, if the gap S increases, it is possible to accurately measure and calculate the variation of the refractive index of the recovered immersion liquid ILr.

Figure 10:
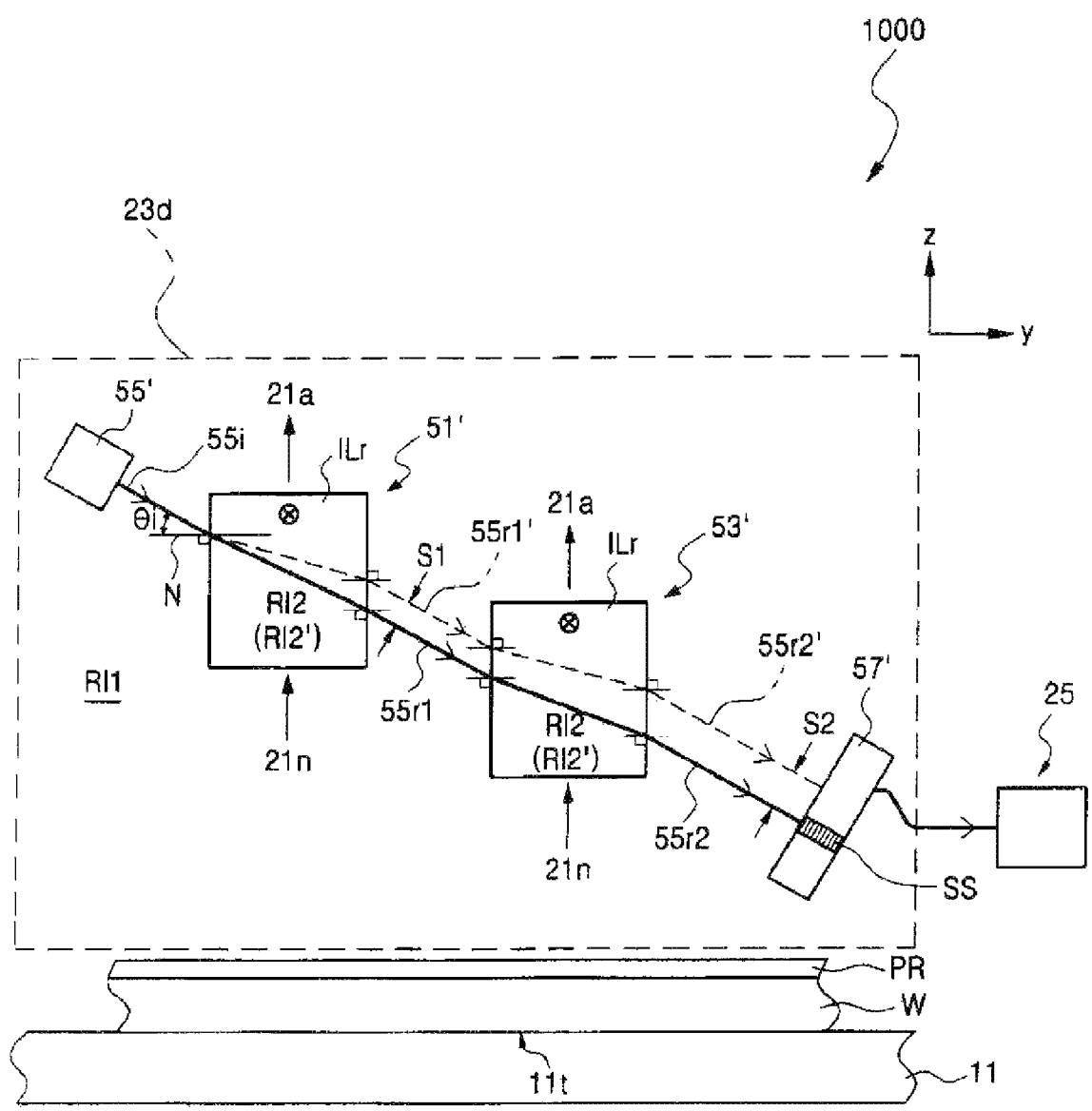
FIG. 10 shows a schematic diagram for another refractive index monitoring unit in accordance with the immersion photolithography apparatus of FIG. 5.

Turning to FIG. 10, an exemplary refractive index monitoring unit, usable in accordance with the immersion photolithography apparatus of FIG. 5, is indicated generally by the reference numeral 1000. Here, a portion 23d of the unit 1000 may be used in the apparatus 500 of FIG. 5. The monitoring unit 1000 includes an auxiliary light source 55', a light detector 57', and first and second recovery conduits 51' and 53'. The auxiliary light source 55', the light detector 57', and the first and second recovery conduits 51' and 53' may be established having a different height from the top surface 11t of the wafer stage 11. Otherwise, the monitoring unit 1000 is similar to the monitoring unit 600 of FIG. 6.

Figure 11:
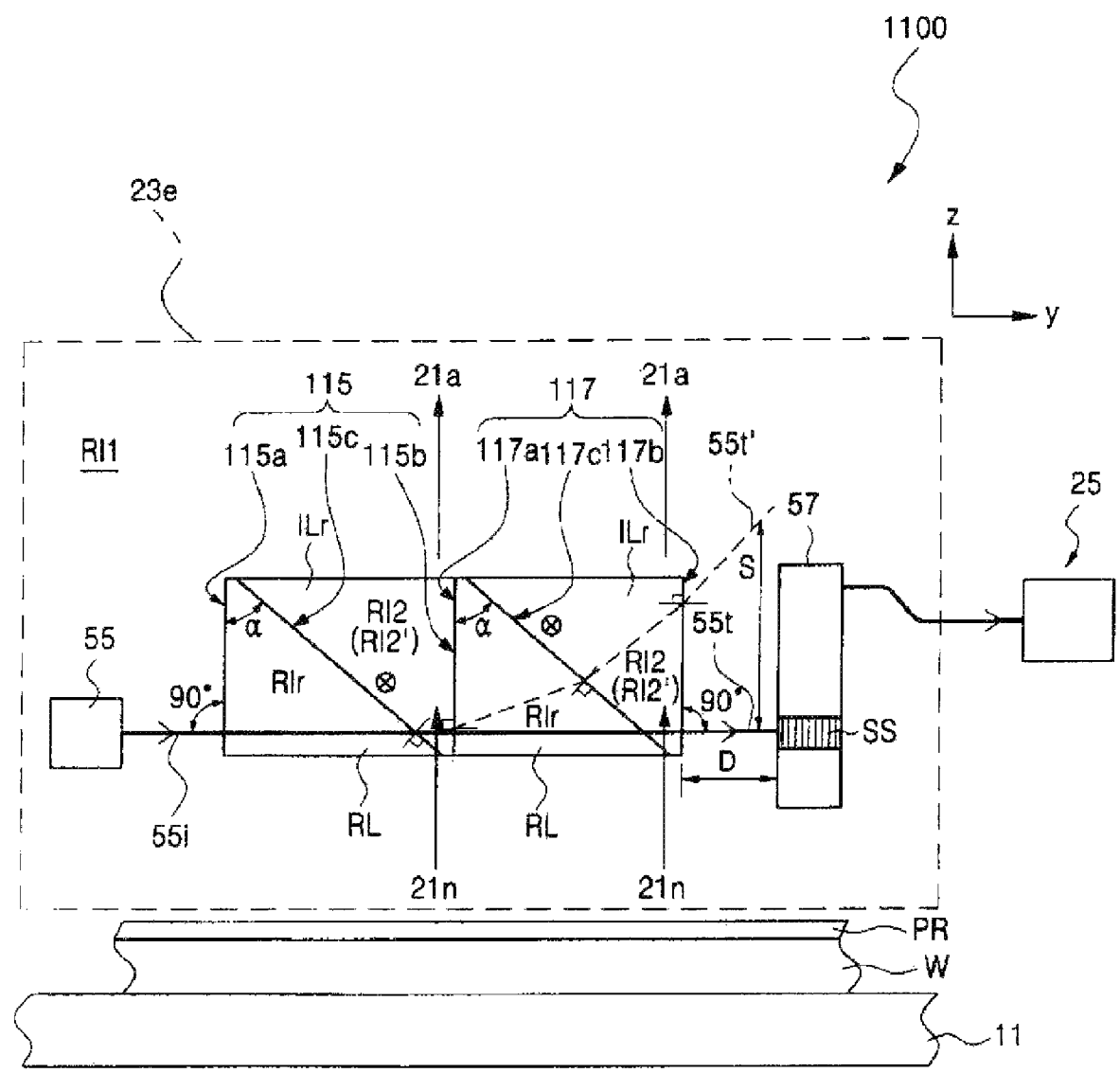
FIG. 11 shows a schematic diagram for another refractive index monitoring unit in accordance with the immersion photolithography apparatus of FIG. 5.

Turning now to FIG. 11, another exemplary refractive index monitoring unit, usable in accordance with the immersion photolithography apparatus of FIG. 5, is indicated generally by the reference numeral 1100. Here, a portion 23e of the unit 1100 may be used in the apparatus 500 of FIG. 5. The monitoring unit 1100 is similar to the monitoring unit 900 of FIG. 9.

The monitoring unit 1100 includes a first conduit cell 115, a second conduit cell 117, first sidewalls 115a and 117a, second sidewalls 115b and 117b, and third sidewalls 115c and 117c. The monitoring portion 23e comprises the first and second cells 115 and 117. The first cell 115 comprises first, second and third sidewalls 115a, 115b and 115c, respectively. The second cell 117 comprises first, second and third sidewalls 117a, 117b and 117c, respectively. An angle α between the first sidewalls 115a, 117a and the third sidewalls 115c, 117c is greater than about 0° and less than about 90°. The first to third sidewalls 115a, 115b, 115c and 117a, 117b, 117c are perpendicular to the wafer stage 11, y-z plane.

A first reference vessel is composed by the first sidewall 115a and the third sidewall 115c, and a first recovery conduit is composed by the second sidewall 115b and the third sidewall 115c. A second reference vessel is composed by the first sidewall 117a and the third sidewall 117c, and a second recovery conduit is composed by the second sidewall 117b and the third sidewall 117c.

The first and second reference vessels are filled with the reference liquid or medium RL having the reference refractive index RIr, and a first portion of the first and second recovery conduits is connected to the recovery pipe 21a. The immersion liquid supplied on the wafer W is recovered through the first and second recovery conduits. When the auxiliary incident light 55i is irradiated vertically toward the first sidewall 115a of the first cell 115, the auxiliary incident light 55i generates the reference output light 55t or the refracted tight 55t' toward the light detector 57 by the same mechanism as explained with respect to FIG. 9.

Figure 12:
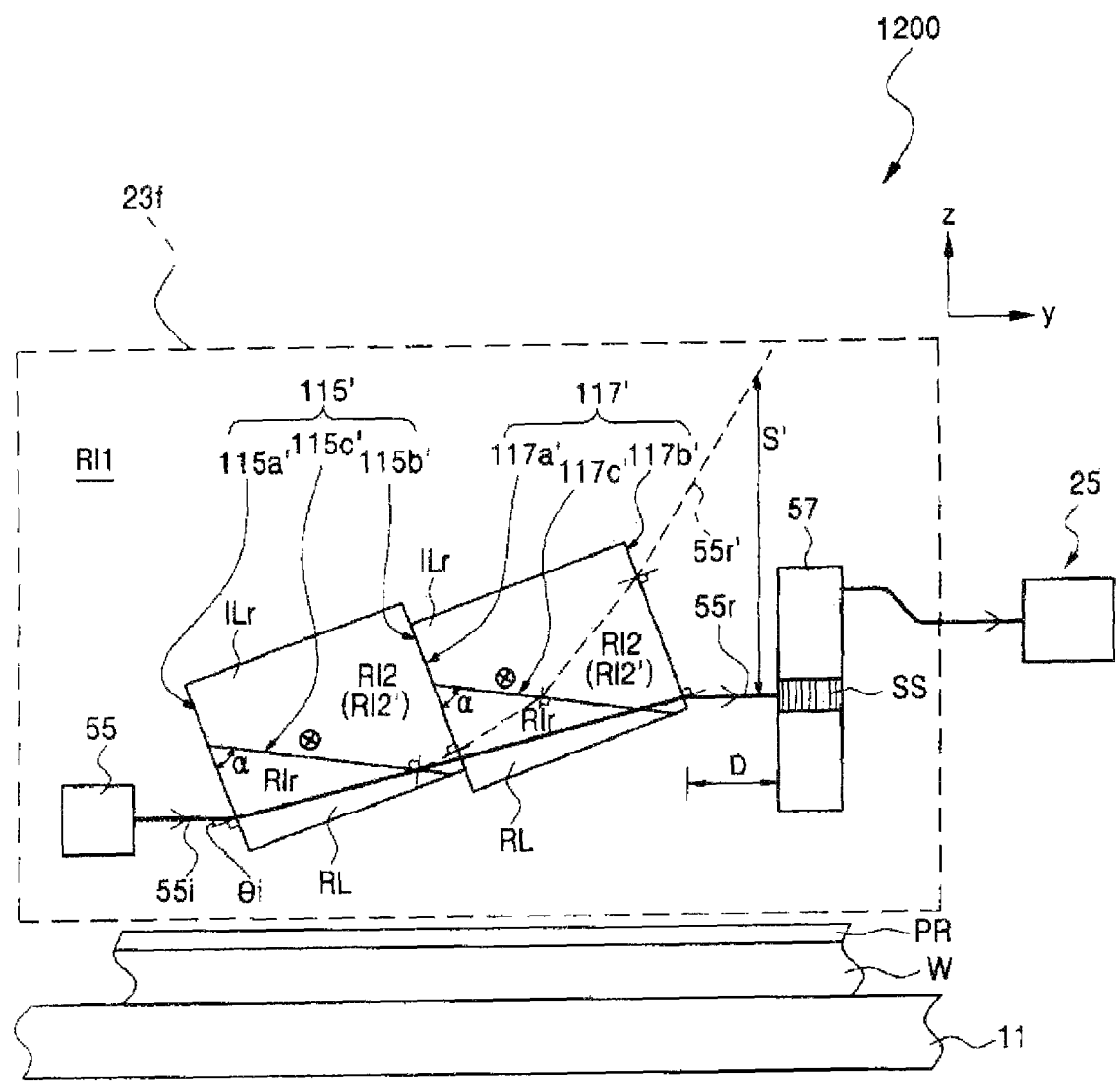
FIG. 12 shows a schematic diagram for another refractive index monitoring unit in accordance with the immersion photolithography apparatus of FIG. 5.

As shown in FIG. 12, yet another exemplary refractive index monitoring unit, usable in accordance with the immersion photolithography apparatus of FIG. 5, is indicated generally by the reference numeral 1200. Here, a portion 23f of the unit 1200 may be used in the apparatus 500 of FIG. 5. The monitoring unit 1200 is similar to the monitoring unit 1100 of FIG. 11.

The monitoring unit 1200 includes first and second conduit cells 115' and 117'. The first cell 115' comprises first, second and third sidewalls 115a', 115b' and 115c', respectively. The second cell 117' comprises first, second and third sidewalls 117a', 117b' and 117c', respectively.

A first reference vessel is composed by the first sidewall 115a' and the third sidewall 115c', and a first recovery conduit is composed by the second sidewall 115b' and the third sidewall 115c'. A second reference vessel is composed by the first sidewall 117a' and the third sidewall 117c', and a second recovery conduit is composed by the second sidewall 117b' and the third sidewall 117c'. The first and second parallel sidewalls 115a', 115b', 117a', 117b' are not perpendicular to the wafer stage 11, y-z plane.

When the auxiliary incident light 55i is irradiated toward the first sidewall 115a' of the nozzle cell 115' substantially in parallel with the direction of the top surface of the wafer stage 11, the incident angle Θi of the auxiliary incident light 55i is above about 0° and below about 90°. The first and second reference vessels are filled with the reference medium RL having the reference refractive index RIr, and a first portion of the first and second recovery conduits is connected to the recovery pipe 21a. The immersion liquid supplied on the wafer W is recovered through the first and second recovery conduits.

When the auxiliary incident light 55i is irradiated toward the first sidewall 115a' of the first nozzle cell 115' at a angle of 0°<Θi<90°, the auxiliary incident light 55i generates the reference output light 55r or the abnormal refracted light 55r' toward the light detector 57 by the same mechanism as explained with respect to FIG. 11. If a distance between the light detector 57 and the second nozzle cell 117' is fixed, a distance S between the reference refracted light 55r and the abnormal refracted light 55r' may be larger than that of FIG. 11 because the auxiliary incident light 55i is irradiated toward the first sidewall 115a' of the first cell 115' at a angle of 0°<Θi<90°, to thereby precisely measure and calculate the refractive index of the immersion liquid ILr recovered in the recovery conduits.

Figure 13:
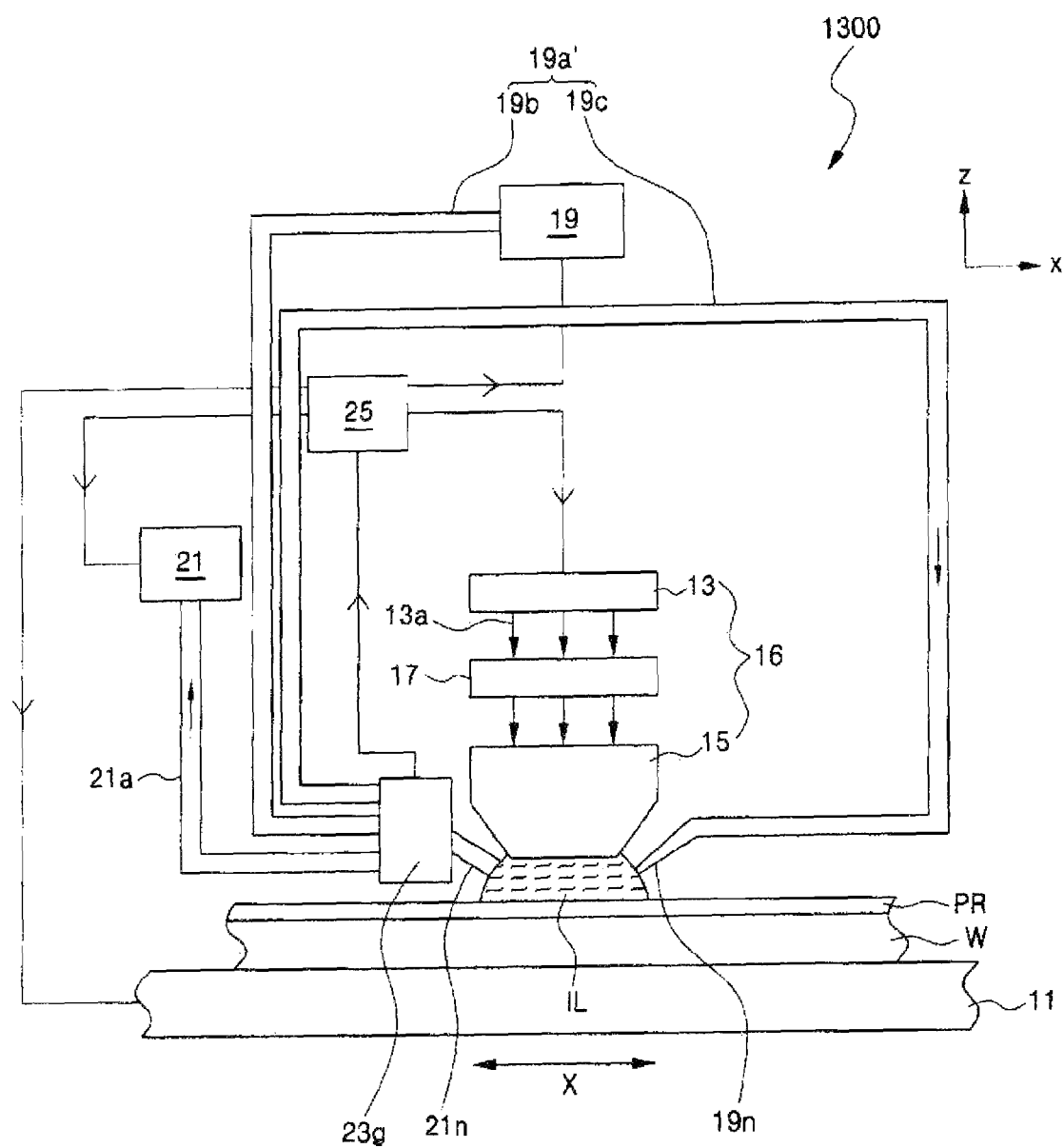
FIG. 13 shows a schematic diagram for another immersion photolithography apparatus in accordance with an exemplary embodiment of the present disclosure.

Turning to FIG. 13, an immersion photolithography apparatus in accordance with another exemplary embodiment of the present disclosure is indicated generally by the reference numeral 1300. The photolithography apparatus 1300 is similar to the photolithography apparatus 500 of FIG. 5. Here, a monitoring portion 23g of the immersion photolithography apparatus 1300 is also connected to the supply pipe. The monitoring unit 23g is connected to the recovery pipe 21a, as well as first and second supply pipes 19b and 19c of the supply pipe 19a'. The first supply pipe 19b is connected to the supply part 19, and transfers the immersion liquid to the monitoring unit 23g. The second supply pipe 19c transfers the immersion liquid in the monitoring unit 23g to the supply nozzle 19n, thereby injecting the immersion liquid onto the wafer through the supply nozzle 19n.

Figure 14:
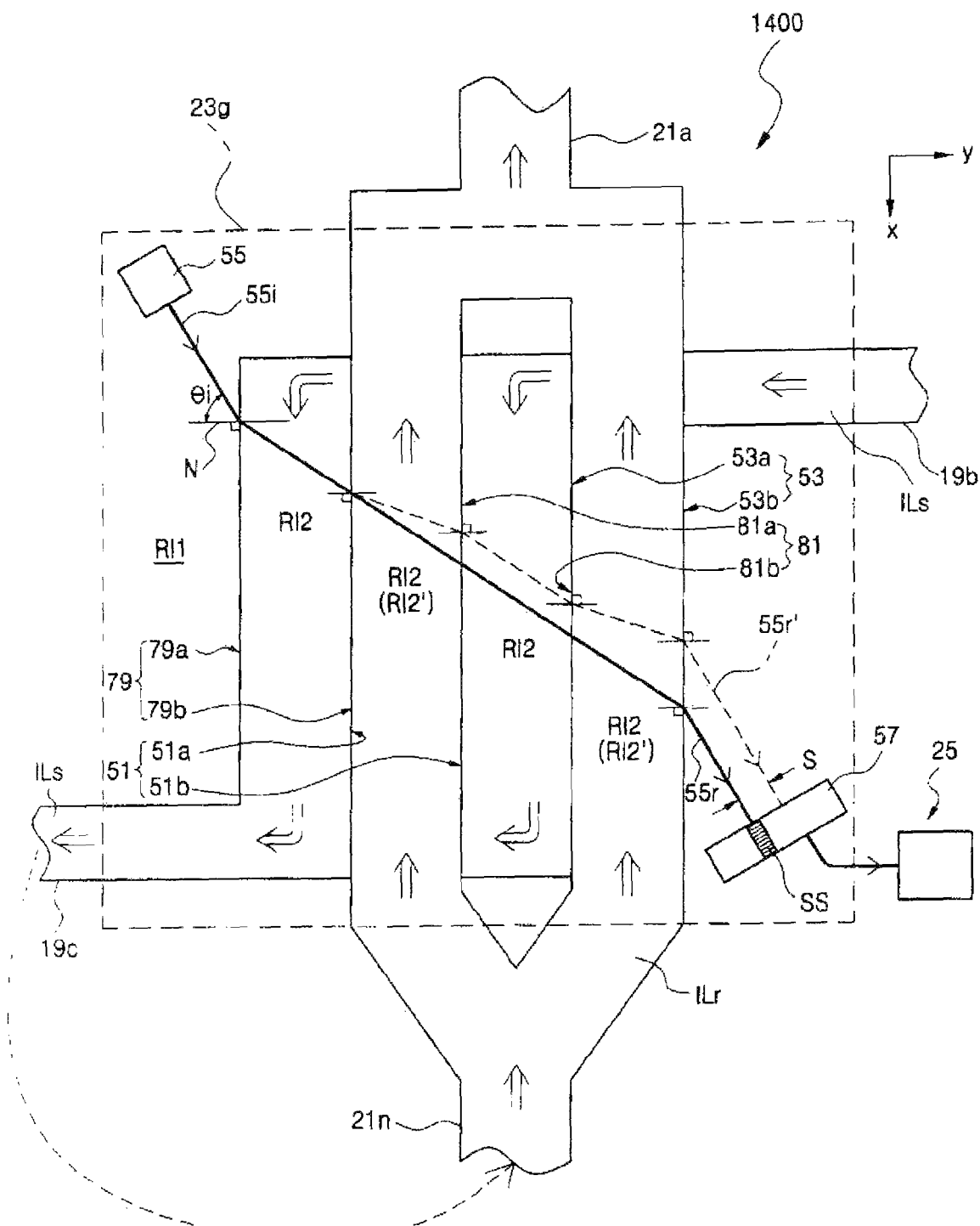
FIG. 14 shows a schematic diagram for a refractive index monitoring unit in accordance with the immersion photolithography apparatus of FIG. 13.

Turning now to FIG. 14, an exemplary refractive index monitoring unit, usable in accordance with the immersion photolithography apparatus 1300 of FIG. 13, is indicated generally by the reference numeral 1400. Here, a portion 23g of the unit 600 may be used in the apparatus 500 of FIG. 5. The monitoring portion 23g is similar to the monitoring portion 23b of FIG. 8.

The monitoring unit 1400 includes first and second recovery conduits 51 and 53, first and second reference conduits 79 and 81, first reference sidewalls 79a and 81a, second reference sidewalls 79b and 81b, first recovery sidewalls 51a and 53a, and second recovery sidewalls 51b and 53b. A common first portion of the first and second reference conduits 79 and 81 is connected to the first supply pipe 19b, and a common second portion of the first and second reference conduits 79 and 81 is connected to the second supply pipe 19c. The supply part 19 provides the immersion liquid ILs on the photo-resist of the wafer W through the first supply pipe 19b, the first and second reference conduits 79 and 81, the second supply pipe 19c, and the supply nozzle 19n.

Thus, the immersion liquid ILs in the reference nozzles 79 and 81 has the same refractive index as the immersion liquid of the supply pipes 19b and 19c. That is, the immersion liquid ILs in the reference nozzles 79 and 81 has the second refractive index RI2 as explained with respect to FIG. 6. Therefore, the immersion liquid ILs in the reference conduits 79 and 81 acts as the reference liquid or medium RL as explained with respect to FIG. 8.

In alternate embodiments, the monitoring unit portions 23c, 23d, 23e and/or 23f of FIGS. 9, 10, 11 and 12, respectively, may also be adapted to the exemplary immersion photolithography apparatus 1300 of FIG. 13. In such cases, the first portions of the reference vessels may be connected to the first supply pipe 19b of FIG. 13, and the second portions of the reference vessels may be connected to the second supply pipe 19c of FIG. 13.

As will be recognized by those skilled in the art, alternate embodiments of the present disclosure may have the refraction light path disposed substantially horizontally, substantially vertically, or at any other desired angle of inclination. A substantially vertical refraction light path may be desirable in low flow rate applications in order to account for a non-homogeneous distribution of contaminants, such as particulates, for example, that may tend to settle out due to gravity. According to the present disclosure, the refraction light path is not constrained by the position of the wafer, for example.

Thus, immersion photolithography embodiments of the present disclosure can measure in real-time the refractive index of an immersion liquid supplied on the wafer. If the immersion liquid from the wafer has a refractive index that deviates from a permitted limit due to contamination, the immersion photolithography process can be controlled, such as by controlling the exposure energy, the exposure time, or the temperature, to thereby prevent a photo-resist pattern from having a non-uniform and/or poor pattern profile.

Although illustrative embodiments have been described herein with reference to the accompanying drawings, it is to be understood that the present disclosure is not limited to those precise embodiments, and that various other changes and modifications may be effected therein by those of ordinary skill in the pertinent art without departing from the scope or spirit of the present disclosure. All such changes and modifications are intended to be included within the scope of the present disclosure as set forth in the appended claims.

What is claimed is:

1. An immersion fluid monitoring apparatus, comprising:
   a light source;
   at least one fluid passageway disposed relative to the light source;
   a light detector disposed on an opposite side of the at least one fluid passageway relative to the light source for measuring a refractive index of a fluid in the at least one fluid passageway, wherein the at least one fluid passageway comprises first and second fluid passageways; and
   a reference medium having a fixed refractive index disposed between at least two of the light source, the first fluid passageway, the second fluid passageway, and the light detector, wherein the reference medium is liquid.

2. An apparatus as defined in claim 1 wherein the at least one fluid passageway is disposed at an angle of between about 20 degrees and about 70 degrees relative to the light source.

3. An apparatus as defined in claim 1 wherein the second fluid passageway is disposed substantially parallel to the first fluid passageway.

4. An apparatus as defined in claim 1 wherein the first and second fluid passageways are interconnected.

5. An apparatus as defined in claim 4 wherein the first and second fluid passageways have a substantially ellipsoid or circular cross-section.

6. An apparatus as defined in claim 4 wherein the first and second fluid passageways have a substantially rectangular or square cross-section.

7. An apparatus as defined in claim 4 wherein the first and second fluid passageways have a substantially triangular cross-section.

8. An apparatus as defined in claim 4, further comprising:
a third fluid passageway disposed between the light source and the first fluid passageway; and
a fourth fluid passageway disposed between the first fluid passageway and the second fluid passageway;
wherein the third and fourth fluid passageways are interconnected.

9. An apparatus as defined in claim 8 wherein the fourth fluid passageway is disposed substantially parallel to the third fluid passageway.

10. An apparatus as defined in claim 8 wherein:
a first sidewall of the first fluid passageway is disposed at a first angle relative to the light source;
a second sidewall of the first fluid passageway is disposed at a second angle relative to the light source;
a first sidewall of the second fluid passageway is coincident with the second sidewall of the first fluid passageway;
a second sidewall of the second fluid passageway is disposed at the first angle relative to the light source;
a first sidewall of the third fluid passageway is coincident with the second sidewall of the second fluid passageway;
a second sidewall of the third fluid passageway is disposed at the second angle relative to the light source;
a first sidewall of the fourth fluid passageway is coincident with the second sidewall of the third fluid passageway; and
a second sidewall of the fourth fluid passageway is disposed at the first angle relative to the light source.

11. An immersion photolithography system having the immersion fluid monitoring apparatus of claim 1, the system further comprising:
a controller coupled in signal communication with the immersion fluid monitoring apparatus for controlling the photolithography system in response to a refractive index of an immersion fluid as measured by the immersion fluid monitoring apparatus;
an immersion hood coupled in fluid communication with the immersion fluid monitoring apparatus;
a wafer stage disposed below the immersion hood for supporting a semiconductor wafer;
a photolithography light source coupled in signal communication with the controller;
a projection tens optically aligned between the photolithography light source and the wafer stage;
an immersion fluid supply nozzle disposed on the immersion hood for supplying an immersion fluid between the projection lens and a layer on the semiconductor wafer; and
an immersion fluid recovery conduit disposed on the immersion hood for recovering the immersion fluid,
wherein the immersion fluid monitoring apparatus is coupled in fluid communication with the recovery conduit.

12. A system as defined in claim 11 wherein the immersion fluid monitoring apparatus is disposed in the recovery conduit.

13. An immersion photolithography system having the immersion fluid monitoring apparatus of claim 8, the system further comprising:
a controller coupled in signal communication with the immersion fluid monitoring apparatus for controlling the photolithography system in response to a refractive index of an immersion fluid as measured by the immersion fluid monitoring apparatus;
an immersion hood coupled in fluid communication with the immersion fluid monitoring apparatus;
a wafer stage disposed within the immersion hood for supporting a semiconductor wafer;
a photolithography light source coupled in signal communication with the controller;
a projection lens optically aligned between the photolithography light source and the wafer stage;
an immersion fluid supply nozzle disposed on the immersion hood for supplying an immersion fluid between the projection lens and a layer on the semiconductor wafer;
an immersion fluid recovery nozzle disposed in the immersion hood for recovering the immersion fluid;
wherein the immersion fluid monitoring apparatus is coupled in fluid communication with each of the immersion fluid supply nozzle and the immersion fluid recovery nozzle.

14. A system as defined in claim 13 wherein:
the first and second fluid passageways of the immersion fluid monitoring apparatus are coupled to one of the immersion fluid supply nozzle and the immersion fluid recovery nozzle; and
the third and fourth fluid passageways of the immersion fluid monitoring apparatus are coupled to the other of the immersion fluid supply nozzle and the immersion fluid recovery nozzle.

15. A system as defined in claim 14 wherein the immersion fluid monitoring apparatus monitors each of the refractive indices of the immersion fluid to the supply nozzle and the immersion fluid from the recovery nozzle, respectively.

16. A system as defined in claim 14 wherein the immersion fluid monitoring apparatus monitors an averaged refractive index between the refractive index of the immersion fluid to the supply nozzle and the refractive index of the immersion fluid from the recovery nozzle.

* * * * *